US005733247A

United States Patent [19]
Fallon

[11] Patent Number: 5,733,247
[45] Date of Patent: Mar. 31, 1998

[54] MR COMPATIBLE PATIENT MONITOR

[75] Inventor: Joseph R. Fallon, Boxford, Mass.

[73] Assignee: Hewlett-Packard Company, Palo Alto, Calif.

[21] Appl. No.: 577,950

[22] Filed: Dec. 20, 1995

[51] Int. Cl.⁶ .................................................. A61B 5/055
[52] U.S. Cl. ............................ 600/410; 324/309; 5/601
[58] Field of Search ..................................... 324/307, 309, 324/318, 322, 200, 260; 128/653.2, 653.1, 696, 687, 716, 731, 901; 600/407, 410, 411, 500, 509, 529, 544; 5/601

[56] References Cited

U.S. PATENT DOCUMENTS

| | | |
|---|---|---|
| 3,847,483 | 11/1974 | Shaw . |
| 4,227,075 | 10/1980 | Holland . |
| 4,737,712 | 4/1988 | Stormont et al. . |
| 4,739,521 | 4/1988 | Akimoto . |
| 4,901,141 | 2/1990 | Costello . |
| 4,991,580 | 2/1991 | Moore . |
| 4,991,587 | 2/1991 | Blakeley et al. ........................ 128/653.2 |
| 5,038,785 | 8/1991 | Blakeley et al. . |
| 5,134,373 | 7/1992 | Tsuruno . |
| 5,209,233 | 5/1993 | Holland et al. . |
| 5,394,873 | 3/1995 | Kraemer et al. ...................... 128/653.2 |
| 5,445,162 | 8/1995 | Ives ........................................ 128/653.2 |
| 5,464,014 | 11/1995 | Sugahara ............................... 128/653.2 |

*Primary Examiner*—Brian L. Casler
*Attorney, Agent, or Firm*—Pamela Lau Kee

[57] ABSTRACT

A MR compatible monitoring system has a fiber optic data link between the patient monitor and the control room display/keyboard in a magnetic resonance imaging suite to allow for continuous monitoring of a patient's vital signs and provides critical care patients with the same diagnostic options as stable patients. The patient monitor is mounted on the far end of a magnetic resonance compatible patient transporter. The patient transporter sends video data and receives control data from the control room. During the imaging, the patient monitor is located within the magnet room. Magnetic resonance imaging systems are very sensitive to radio frequency interference (RFI) from other equipment and may produce image artifacts because of this interference. Using a fiber optic data link between the patient monitor near the magnet and the control room will minimize the potential RFI.

11 Claims, 4 Drawing Sheets

MR COMPATIBLE PATIENT MONITOR

FIELD OF THE INVENTION

This invention relates to a patient monitoring system that is compatible with an environment having strong electrical and magnetic field levels, such as that found near a magnetic resonance imaging system.

BACKGROUND OF THE INVENTION

Although a patient may physically appear to be in good health, cardiovascular conditions, such as stenosis, are difficult for a physician to confirm with just his five senses and training. Preventive care measures cannot be suggested because the physician has insufficient data to make a diagnosis. A magnetic resonance (MR) scanner is a medical diagnostic tool which can provide this data by imaging the anatomy, as well as performing in-vivo, non-invasive, spectroscopic analysis of stable patients. The patient is positioned in a homogeneous polarizing magnetic field $B_o$ and then briefly excited by irradiation with a radio frequency at the Larmor frequency ($f=yB_o$, where y=42.57 MHZ/Tesla). The MR signals emanating from the patient in response to the stimulus are observed. The MR scanner includes a magnet, frequently of solenoidal design, which produces the polarizing magnetic field, typically between 0.2 and 2.0 Tesla. The bore of the magnet has a large diameter to accommodate the RF, gradient, and shim coil assemblies, as well as the patient. A sliding patient tray is used to position the patient within the bore. The patient tray is longitudinally aligned with the magnet at a fixed height for patient positioning.

If a patient undergoing a MR scan becomes critically ill, he must be quickly moved outside of the MR scanning room. This is necessary because most of the support equipment, (i.e. a defibrillator) used for critical patient care is not compatible with the MR scanning room environment. In the MR scanning room, there are strong magnetic and electric fields which may adversely affect the operation of the support equipment. Conversely, the support equipment may adversely affect the operation of the MR scanner.

The strong magnetic and electric fields found in the MR scanning room make it difficult to monitor a patient's vital signs. Because of these strong fields, the patient's vital signs are sometimes observed on monitoring equipment located externally to the MR scanning room. Long cables are then required to connect the patient to the monitoring equipment. These cables are subjected to the strong electric and magnetic fields found in the MR scanning room. These conditions place extreme demands on the shielding properties of the interconnecting cables. The length of these cables may introduce unacceptable signal loss and degradation of the associated physiological parameter measurements. In addition, these cables tend to drape across the patient as they exit the bore of the magnet. This cable placement poses a potential interference to quickly evacuating a patient from the MR scanner in an emergency situation. In addition, the cables are subject to damage should they be run over by the patient transporter during the movement of the patient. As a result of these issues, critical care patients are not always provided with continuous monitoring of their vital signs during MR scanning.

A patient monitoring system that is compatible with the MR scanning room environment and does not impede the transport of critical patients out of the scan room is therefore desirable.

SUMMARY OF THE INVENTION

A MR scanning room compatible patient monitoring system allows continuous monitoring of a patient's vital signs during the MR scans. This monitoring system may be mounted on the far end of the MR compatible patient transporter. The transporter is used to transfer the patient to and from the magnet in the MR scanning room. A fiber optic data link connects between the patient monitor, the MR scanner, and the control room.

The MR compatible patient monitoring system has an shielded enclosure that acts as a Faraday shield. The patient monitor's microprocessor, LCD display, a control panel, a magnetic field sensor, a fiber optic data link, and at least one physio module are contained within the shielded enclosure. A clinician can observe the patient's vital signs on the LCD display and make any adjustments via the control panel.

DETAILED DESCRIPTION OF THE PREFERRED EMBODIMENTS

Figure 1:
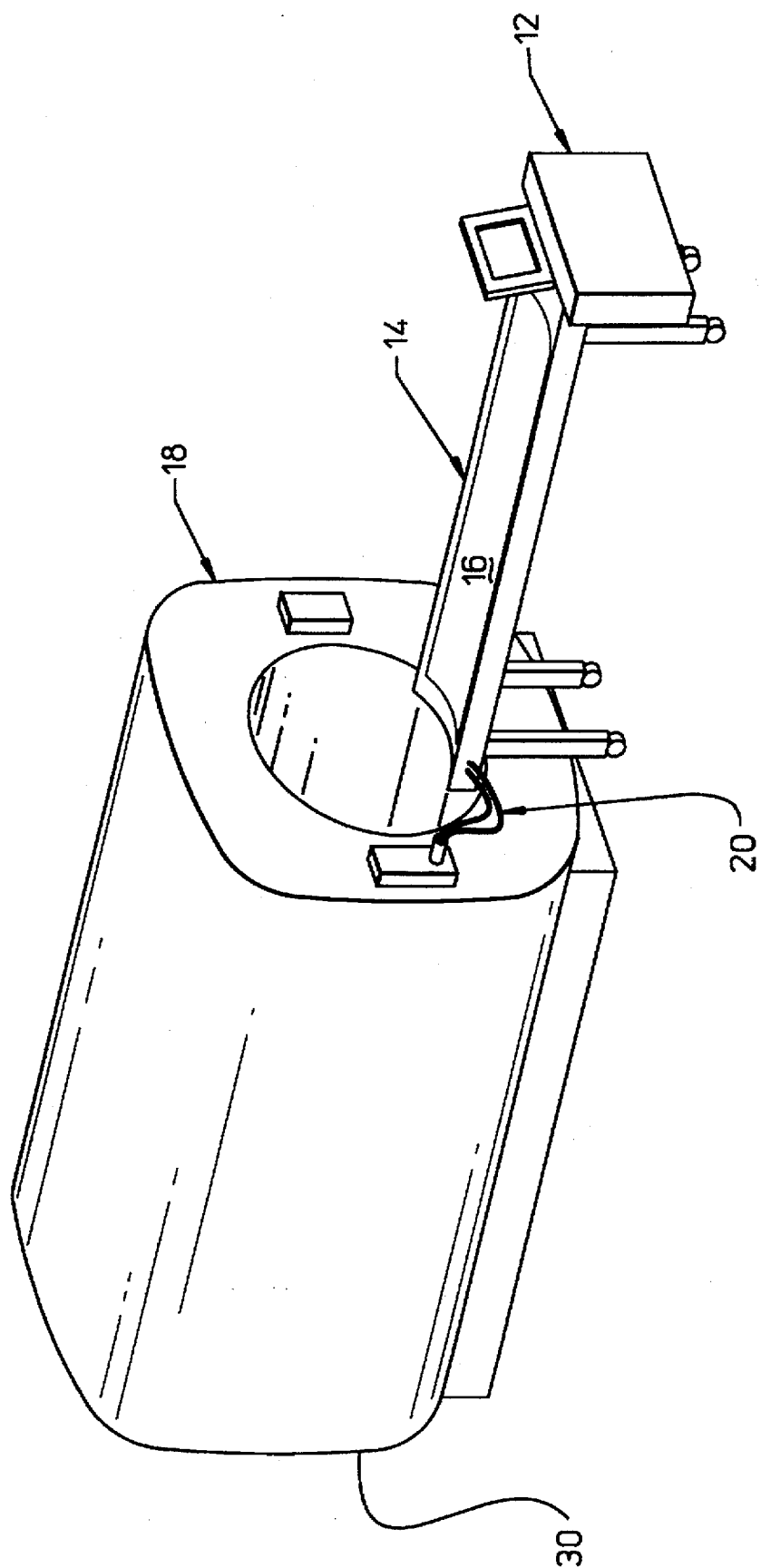
FIG. 1 illustrates a MR compatible patient monitoring system.

FIG. 1 illustrates a MR compatible patient monitoring system 10. A patient monitor 12 is mounted at one end of a patient transporter 14. The patient transporter 14 has a patient tray 16 which slides into a bore of a magnet 18. A system interconnect 20 connects between the patient transporter 14 and the magnet 18.

Figure 2:
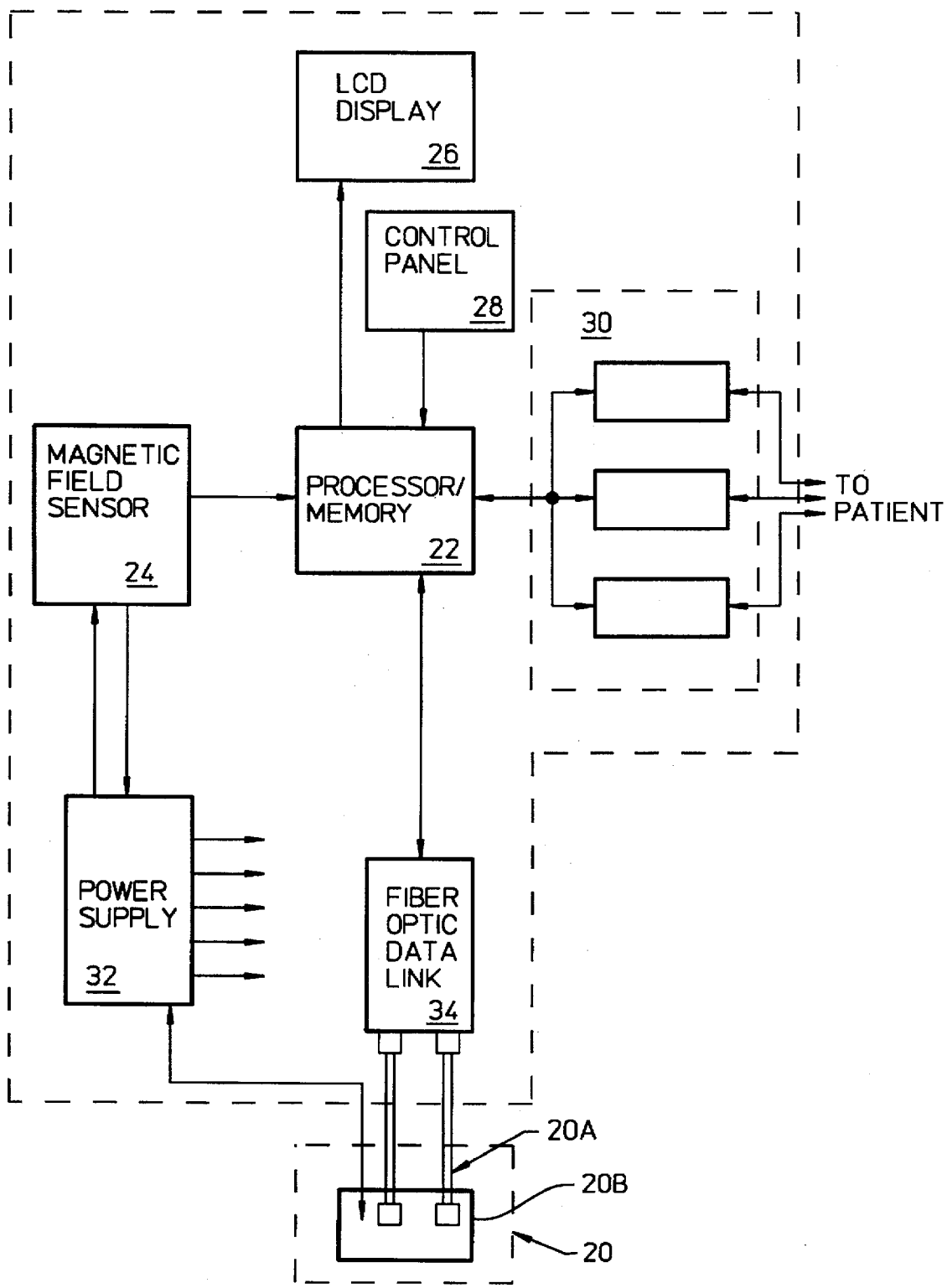
FIG. 2 illustrates a functional block diagram for the MR compatible patient monitoring system shown in FIG. 1.

FIG. 2 illustrates a functional block diagram for the MR compatible patient monitoring system 10 shown in FIG. 1. A processor/memory block 22 is connected to a magnetic field sensor 24, a LCD display 26, a control panel 28, physio module block 30, power supply 32, and a fiber optic data link 34. The magnetic field sensor 24 is further connected to the power supply 32. The power supply 32 and the fiber optic link 34 are connected to a system interconnect 20. All of the aforementioned components are contained within a shielded enclosure 36.

The processor/memory block 22 provides the central computing and control function required for the monitoring system 10. This includes the acquisition and processing of the patient's physiological signals, the control and verification of the various subsystems as well as the display 26 and user control panel 28. In this embodiment, this block is based on a high performance 32 bit microprocessor. The associated program and data memory requirements are provided by the processor/memory block's RAM and EEPROM memory arrays.

The magnetic field sensor 24 senses the ambient magnetic field that the patient monitor is operating in. It calculates the absolute magnitude of the ambient field by using a Cartesian coordinate field sensor. The absolute magnitude of the ambient field is then compared against three threshold values. As the patient transporter 14 is moved through the MR scanner room, the patient monitor may be subject to magnetic field levels which would adversely affect its operation. The magnetic field sensor 24 warns the user by visual and audio indicators if the ambient field strength is approaching the level (the first threshold) at which operation of the monitor would be affected. If the field continues to increase and then exceeds the second threshold, the magnetic field sensor 24 will disable the operation of the patient monitor until the field level falls below a preset value (the third threshold). The sensor 24 continues to provide the user with an indication of the ambient field level even when the monitor is disabled.

The power supply 32 provides the power requirements for the patient monitor. In this embodiment, the power supply 32 consists of a DC-to-DC converter, battery charger, and rechargeable battery. The DC-to-DC converter converts the battery voltage into the various voltages required by the patient monitor. The battery charger maintains the battery's charge when the monitor is connected to either the MR scanner or to an external charging port.

The fiber optic data link block 34 provides the data and control link between the patient monitor and the MR scanner. The fiber optic data link block 34 supports remote displays and control of the patient monitor, as well as the exchange of data, control and status information between the MR scanner and the patient monitor. The block features a high speed, duplex long wavelength fiber optic transceiver. The interface between the fiber optic transceiver and the processor subsystem is handled by a set of specialized receive and transmit integrated circuits. This chip set provides the parallel-to-serial and serial-to-parallel data conversion, data formatting, clock recovery, and link control logic.

The system interconnect 20 provides the connection between the patient monitor and the MR scanner. It consists of an umbilical cable 20A and a connector 20B featuring both electrical and optical contacts. The cable 20A is routed through the patient transporter 14 where it is then mated to the matching receptacle on the MR scanner 18.

The umbilical cable 20A consists of a duplex fiber optic cable pair and a pair of electrical conductors surrounded by a common PVC outer jacket. Each of the fiber optic cables has a core diameter of 62.5 micrometers and a cladding diameter of 125 micrometers. These fiber optic cables are used to support the duplex data and control link between the patient monitor and the MR system. The electrical conductors are used to supply the patient monitor's DC to DC converter/battery charger.

The connector 20B features a pair of fiber optic contacts. These contacts are capable of repeated mate/demate cycles while maintaining the required optical performance. The connector body is made of a structural plastic, i.e. PEEK, to minimize the production of particulate during the mate/demate cycle. These particulates and environmental factors, such as dirt, dust, and smoke, could reduce or obscure the transmission of light through the connector. To safeguard against the environment factors, the connector uses a sealing cap that retracts during the mating cycle. The matching receptacle on the MR scanner uses a set of shutter doors which prevent degradation of the contacts due to environmental factors. The shutter doors swing aside during the mating cycle.

In one embodiment, the system connector 20B is a cable/connector assembly that the user can plug into a matching receptacle on the MR scanner once the patient transporter has "docked" with the MR scanner. The user will unplug the cable when the transporter has been "undocked". The cable is managed by a cable retraction system on the patient transporter to prevent the cable from damage when not in use. Alternately, the system connector can be part of a docking mechanism which automatically makes and breaks contact as the transporter is "docked" and "undocked" with the MR scanner.

The LCD display 26 presents the patient parameter data to the clinicians. An LCD type display was selected because the strong magnetic fields in proximity of the MR scanner make use of a CRT type difficult.

The control panel 28 allows the user to control the operation of the patient monitor. It contains an array of keys and indicator LEDs.

The shielded enclosure 36 serves two major functions. The first is to reduce the radiated emissions from the patient monitor internal circuits to a level where they will not cause any interference to the operation of the MR scanner. The second function that it serves is to reduce the internal level of the ambient electrical fields.

Figure 3:
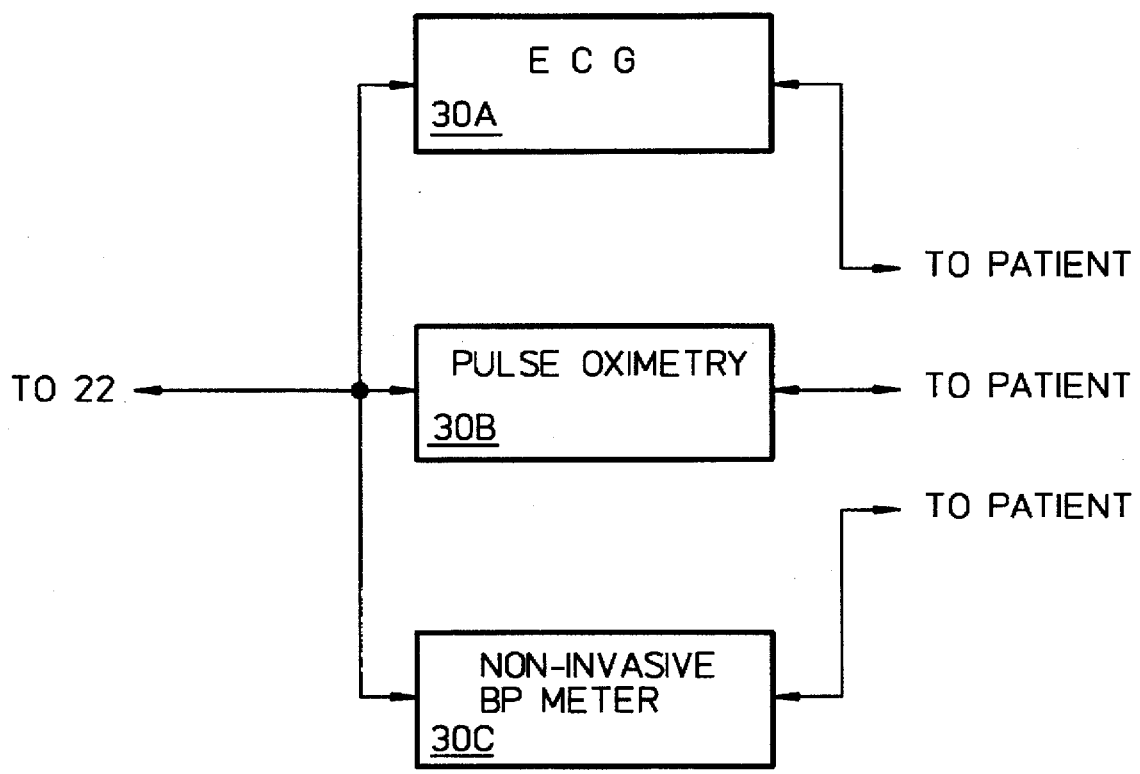
FIG. 3 is a system diagram of the physio-module block shown in FIG. 2.

FIG. 3 is a system diagram of the physio-module block 30 shown in FIG. 2. The physiomodules support the acquisition and conditioning of several patient parameters. Three such modules, such as 30A-C, are shown by way of illustration.

The ECG physio-module 30A handles the patient's ECG signal. It contains isolation amplifiers, filter states, analog to digital convertors, and adaptive filtering stages. The adaptive filters use knowledge of the operation of the MR scanner to filter the gradient noise components from the ECG signal.

The pulse oximeter block 30B handles the patient pulse oximeter parameter. It uses a transducer which uses fiber optic cables to send the light from a set of visible and infrared light sources to the measuring site and to return the transmitted component to a photo detector. This transducer is usually applied to a finger and the ratio of transmission of the visible and infrared light sources to the finger is measured. This ratio is used to calculate the percentage of oxygenated hemoglobin for the patient. The block contains a light source driver stage, photo detector amplifier, and filter stages, and analog to digital convertors.

The non-invasive sphygmomanometer 30C handles the measurement of the patient's blood pressure. It uses an inflatable cuff which is applied to the patient's arm or leg. The cuff is connected to the monitor via a non-conductive air tube. The block contains the cuff pump, pressure sensor, and analog to digital convertor. The cables which are used to connect the patient to the three parameter blocks are integrated into the patient transporter with a cable management system. This system protects the cables during transport to and from the MR scanner and while the patient table is sliding in and out of the magnet.

Figure 4:
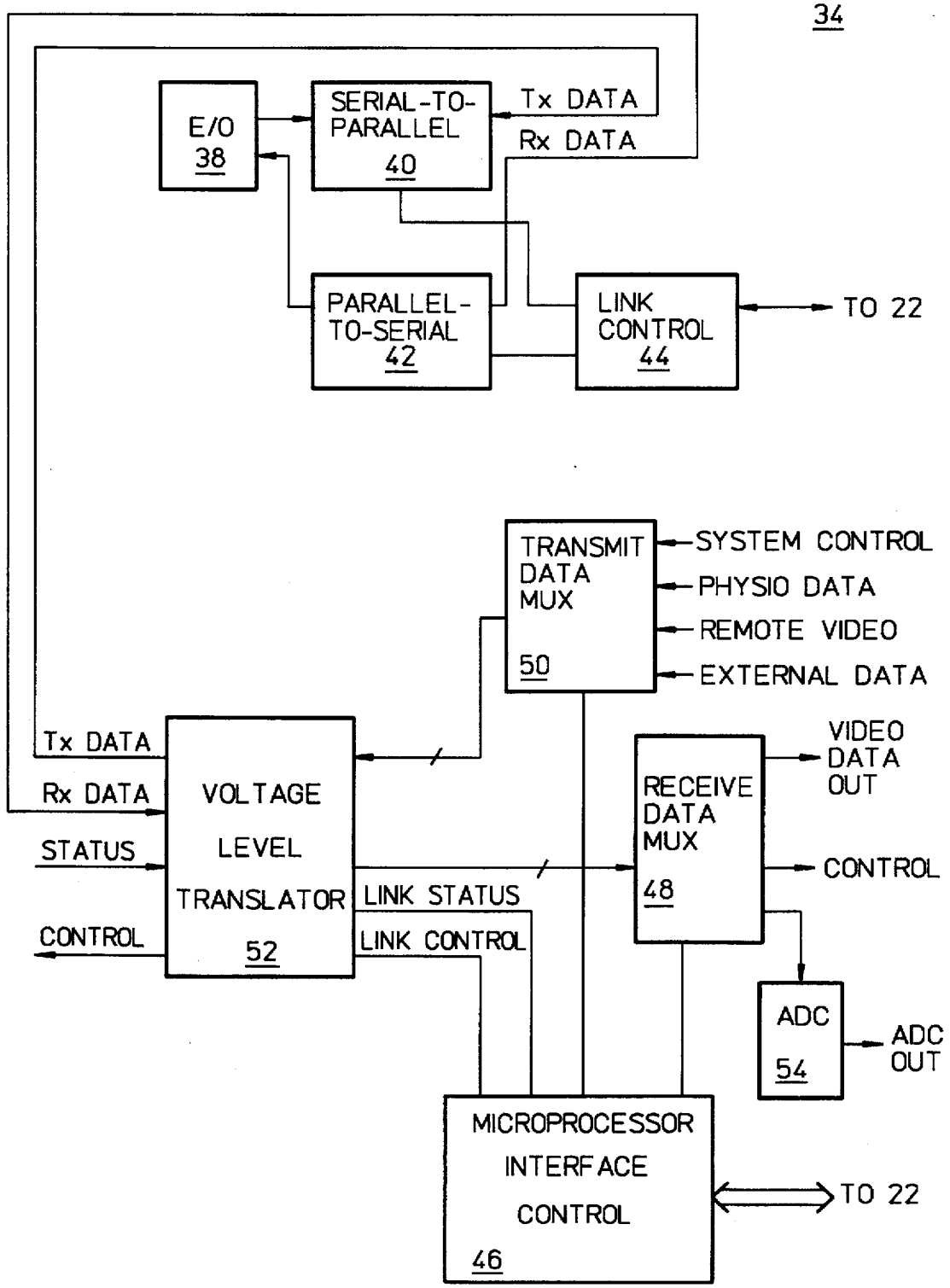
FIG. 4 illustrates the fiber optic data link shown in FIG. 1.

FIG. 4 illustrates the fiber optic data link 34 shown in FIG. 1. An Electrical/Optical (EO) block 38 is connected to a Serial-to-Parallel block 40 and a Parallel-to-Serial block 42. A Link Control block 44 is connected to the Serial-to-Parallel block 40 and the Parallel-to-Serial block 42. The Link Control block 44 is further connected to a Microprocessor Interface Controller 46. The Microprocessor Interface Controller 46 is further connected to a Receive Data Demultiplexor 48, a Transmit Data Multiplexor 50, and a Voltage Level Translator block 52. The Voltage Level Translator block 52 is further connected to the Receive Data Demultiplexor 48 and the Transmit Data Multiplexor 50. The Receive Data Demultiplexor 48 is further connected to an Analog-to-Digital Converter block 54.

The EO block 38 converts the incoming optical signal to a serial electrical signal and conversely, the serial electrical signal into an optical output signal. The optical signals are coupled to and from a duplex fiber optic cable. In this embodiment, this block is comprised of an Hewlett-Packard HFBR 5205 Multi-mode Fiber Transceiver that operates at a wavelength of 1300 nm.

The Serial-to-Parallel block 40 converts the serial electrical output signal from the EO block into a parallel digital signal. This block contains the clock recovery, signal detect, and framing circuits.

The Link Control block 44 controls the operation of the fiber link. Upon being connected to the fiber optic link cable through the system interconnect, it outputs a series of unique data packets which are designed to facilitate synchronization with the matching fiber link subsystem at the other end of the fiber cable. It also initiates a search for these synchronization packets on the incoming optical path via examining the EO serial output. Upon detection of the synchronization packets, it enables data to be sent to and received from the link. The link control block 44 monitors the operation of the operation of the link and flags any data errors. For non-recoverable errors, it disables local use of the link and periodically attempts to re-establish connection.

In this embodiment, the Serial-to-Parallel 40, Parallel-to-Serial 42, and the Link Control 44 blocks were implemented using the Hewlett-Packard HDMP1012 and HDMP1014 integrated circuit chipset.

The Voltage Level Translator block 52 bidirectionally translates the data, control, and status signals from one set of logic levels to another. In this embodiment, the logic voltage levels are TTL and PECL.

The Transmit Data Multiplexor 50 organizes the parallel data which is to be sent as output on the fiber link. There are several sources for this data. These include the remote display video data, physio data, and monitor status data.

The Receive Data Demultiplexor 48 inputs the received and translated parallel data from the Serial-to-Parallel block 40. The data is demultiplexed and sent to a number of outputs. The outputs include video update data, remote keyboard and system control data and external data.

The Analog-to-Digital Converter block 54 converts the externally received digital data via the link into an analog signal. This signal is output to an analog multiplexor and it can be used by the patient monitor to provide local audio annunciation, as well as an analog source useful for signal injection and system verification.

The Microprocessor Interface Controller block 46 provides two major functions. The first function is to support the patient monitor interface to the fiber data link. It contains several state machine logic circuits which in conjunction with the control logic of the Link Control block 44, determine the operation of the fiber link. It coordinates the synchronization of the operation of the Transmit Data Multiplexor 50 and the Receive Data Demultiplexor 48 to ensure the correct data position in the multiplexing cycle. The second function of this block is to support access to the fiber link and it's operation by the patient monitor resident microprocessor. It provides an interface that appears to the microprocessor as a series of registers. Read and write cycles to these registers allow the microprocessor to send and receive data, control the mode of operation as well as to examine the status of the fiber data link.

I claim:

1. A MR compatible patient monitoring system for connecting to a remote terminal comprising:
   a patient transporter;
   a shielded enclosure attached to the patient transporter;
   a system interconnect, positioned external to the the shielded enclosure;
   a microprocessor, positioned within the shielded enclosure;
   a LCD display, positioned within the shielded enclosure;
   a control panel, positioned within the shielded enclosure;
   characterizing means for characterizing a magnetic field;
   a MR immune transceiver positioned within the shielded enclosure, connecting to the system interconnect; and
   a physiomodule, being operative to monitor a patient, positioned within the shielded enclosure; wherein the LCD display, the control panel, the characterizing means, the MR immune transmission means, and the physiomodule are connected to the microprocessor.

2. A MR compatible patient monitoring system, as defined in claim 1, wherein the characterizing means includes a magnetic field sensor and a magnetic field indicator, connected to the magnetic field sensor, that indicates the magnetic field near the MR scanner.

3. A MR compatible patient monitoring system, as defined in claim 2, the magnetic field indicator further includes a visual indicator.

4. A MR compatible patient monitoring system, as defined in claim 2, the magnetic field indicator further includes an auditory indicator.

5. A MR compatible patient monitoring system, as defined in claim 2, the magnetic field indicator further includes a monitor protector that is operative to disable the patient monitoring system when a selected threshold is exceeded to prevent damage to the patient monitoring system.

6. A MR compatible patient monitoring system, as defined in claim 1, wherein the system interconnect is a manual cable connector assembly.

7. A MR compatible patient monitoring system, as defined in claim 6, where the characterizing means is a magnetic field sensor.

8. A MR compatible patient monitoring system, as defined in claim 6, wherein the system interconnect is a retracting cable assembly.

9. A MR compatible patient monitoring system, as defined in claim 1, wherein the MR immune transmission means is a fiber optic data link.

10. A MR compatible patient monitoring system, as defined in claim 1, wherein the MR immune transmission means is a duplex microwave link.

11. A MR compatible patient monitoring system, as defined in claim 1, wherein the MR immune transmission means is a duplex infra-red link.

* * * * *